(12) United States Patent  
Suzuki

(10) Patent No.: US 12,286,644 B2  
(45) Date of Patent: Apr. 29, 2025

(54) CARDIOSPHERE-DERIVED CELL SHEET AND METHODS OF MAKING AND USING THE SAME

(71) Applicant: Gen Suzuki, Tokyo (JP)

(72) Inventor: Gen Suzuki, Tokyo (JP)

( * ) Notice: Subject to any disclaimer, the term of this patent is extended or adjusted under 35 U.S.C. 154(b) by 475 days.

(21) Appl. No.: 16/957,860

(22) PCT Filed: Dec. 21, 2018

(86) PCT No.: PCT/US2018/067342  
§ 371 (c)(1),  
(2) Date: Jun. 25, 2020

(87) PCT Pub. No.: WO2019/133535  
PCT Pub. Date: Jul. 4, 2019

(65) Prior Publication Data  
US 2021/0054341 A1 Feb. 25, 2021

Related U.S. Application Data

(60) Provisional application No. 62/610,721, filed on Dec. 27, 2017.

(51) Int. Cl.  
*C12N 5/077* (2010.01)  
*A61F 2/958* (2013.01)  
(Continued)

(52) U.S. Cl.  
CPC ............ *C12N 5/0657* (2013.01); *A61F 2/958* (2013.01); *A61L 27/3625* (2013.01);  
(Continued)

(58) Field of Classification Search  
CPC .............. C12N 5/0657; C12N 2500/38; C12N 2501/115; C12N 2513/00; A61F 2/958;  
(Continued)

(56) References Cited

U.S. PATENT DOCUMENTS

2009/0233356 A1   9/2009  McAllister et al.  
2011/0256105 A1*  10/2011 Marban ..................... A61P 9/00  
424/94.63  
(Continued)

FOREIGN PATENT DOCUMENTS

CA        2702173 A1 *  4/2009  ........... A61L 27/222  
JP     2010-268715 A    12/2010  
(Continued)

OTHER PUBLICATIONS

Cho "Secondary Sphere Formation Enhances the Functionality of Cardiac Progenitor Cells." The American Society of Gene and Cell Therapy, vol. 20, No. 9. 1750-1766, Sep. 2012 (Year: 2012).*

(Continued)

*Primary Examiner* — Blaine Lankford  
*Assistant Examiner* — Lauren K Van Buren  
(74) *Attorney, Agent, or Firm* — Oblon, McClelland, Maier & Neustadt, L.L.P.

(57) ABSTRACT

A method of making a cell sheet comprising secondary spheroids, including (a) obtaining cardiosphere-derived cells; (b) cultivating the cardiosphere-derived cells for a first period of time in a first media comprising at least one of an ascorbic acid and an analog thereof, to form secondary spheroids; (c) transferring an amount of the spheroids formed in step (b) into a mold; (d) culturing the secondary spheroids for a second period of time in a second media comprising at least one of the ascorbic acid and an analog thereof, wherein the at least one of the ascorbic acid and an analog thereof is present in an amount effective to promote a formation of an extracellular matrix; and (e) culturing a product obtained in step (d) for a third period of time, in the absence of the at least one of the ascorbic acid and an analog thereof.

12 Claims, 29 Drawing Sheets

(51) Int. Cl.
  *A61L 27/36* (2006.01)
  *A61L 27/38* (2006.01)
  *A61L 27/54* (2006.01)

(52) U.S. Cl.
  CPC ....... *A61L 27/3834* (2013.01); *A61L 27/3895* (2013.01); *A61L 27/54* (2013.01); *A61L 2430/20* (2013.01); *C12N 2500/38* (2013.01); *C12N 2501/115* (2013.01); *C12N 2513/00* (2013.01)

(58) Field of Classification Search
  CPC ............ A61L 27/3625; A61L 27/3834; A61L 27/3895; A61L 27/54; A61L 2430/20
  See application file for complete search history.

(56) References Cited

U.S. PATENT DOCUMENTS

2015/0368618 A1* 12/2015 Nadal-Ginard ...... C12N 5/0692
  435/375
2016/0108365 A1* 4/2016 Marbán ................ C12N 5/0657
  435/375

FOREIGN PATENT DOCUMENTS

JP       2010-270156 A    12/2010
WO    WO-2010118059 A1 * 10/2010  ........... C12N 5/0657

OTHER PUBLICATIONS

Suzuki et al. "Global Intracoronary Infusion of Allogenic Cardiosphere-Derived Cells Improves Ventricular Function and Stimulates Endogenous Myocyte Regeneration throughout the Heart in Swine with Hibernating Myocardium" Nov. 2014, vol. 9, Issue 11 (Year: 2014).*

Tsutumi et al. "Effects of L-ascorbic acid 2-phosphate magnesium salt on the properties of human gingival fibroblasts" J Peridontal Res. Apr. 2012; 47(2): 262-271. (Year: 2012).*

Tung et al. "High-throughput 3D spheroid culture and drug testing using a 384 hanging drop array" Analyst, Feb. 7, 2011; 136(3): 473-478. (Year: 2011).*

International Search Report (PCT/US2018/067342).

Japanese Notice of Reasons for Refusal mailed on Mar. 14, 2023 issued in Japanese Patent Application No. 2020-555727 filed Dec. 21, 2018, with English Translation, total 9 pages.

* cited by examiner

GATA4: 37±5%

Ki67: 21±3%

| | |
|---|---|
| CD31: endothelial progenitor cell | (+) |
| von Willebrand Factor: endothelial cell | (-) |
| α-Smooth Muscle Actin | (-) |
| CD117: stem cell marker | (+) |
| CD90: mesenchymal stem cell marker | (+) |
| GATA4: early myocyte marker | (+) |
| Ki67: cell cycling | (+) |
| Collagen I & III | (+) |
| Fibrosis | (-) |
| Cardiac Troponin I | (-) |
| TUNEL: apoptosis | (-) |

FIG.11F

CARDIOSPHERE-DERIVED CELL SHEET AND METHODS OF MAKING AND USING THE SAME

CROSS REFERENCE TO RELATED APPLICATIONS

This application claims priority under 35 U.S.C. 119 based upon U.S. Provisional Patent Application Ser. No. 62/610,721, filed on Dec. 27, 2017. The entire disclosure of the aforesaid application is incorporated herein by reference.

FIELD OF THE INVENTION

The present invention relates to cardiosphere-derived cell sheets, and methods of producing and using the same.

BACKGROUND OF THE INVENTION

Adult stem cells (i.e., those derived from bone marrow, adipose tissue, heart (cardiospheres), and the like) provide promising therapies for regenerating dead myocardium and improving left ventricular (LV) functioning. It has been demonstrated that myocardium regeneration induced by cardiosphere-derived cells (CDCs) mainly results from CDC secretions of paracrine factors, including growth factors, cytokines and microRNAs (examples include HGF, IGF-1, VEGF and SDF-1), rather than from direct differentiation of CDCs to de novo cardiac cells. That is, CDCs secrete paracrine factors which reduce scar volume and myocyte apoptosis, increase myocyte proliferation, and activate endogenous cardiac stem cells into producing new myocytes. Accordingly, the modulation of paracrine factors from stem cells plays an important role in cardiac regeneration in post-myocardial infarctions.

Unfortunately, the therapeutic benefits of adult stem cells in patients with infarcted myocardia have been modest at best, due to the transient paracrine effects associated with the low retention of injected stem cells. Within minutes of intra-myocardial or intracoronary stem cell injection, the majority of the cells (~85% of the cells) are washed out, and only 1-2% of the cells are retained in the heart at 1-month post-injection.

SUMMARY OF THE INVENTION

In light of the above problems, a purpose of the present invention is to employ bioengineering technologies to provide thin, flexible and durable cell sheets containing viable stem cells, for optimizing cell retention as well as prolonging paracrine secretion.

According to a first embodiment of the present invention for achieving the purpose described above, there is provided:
a method of making a cell sheet comprising secondary spheroids, including:
(a) obtaining cardiosphere-derived cells;
(b) cultivating the cardiosphere-derived cells for a first period of time in a first media comprising at least one of an ascorbic acid and an analog thereof, to form secondary spheroids;
(c) transferring an amount of the spheroids formed in step (b) into a mold;
(d) culturing the secondary spheroids for a second period of time in a second media comprising at least one of the ascorbic acid and an analog thereof, wherein the at least one of the ascorbic acid and an analog thereof is present in an amount effective to promote a formation of an extracellular matrix; and
(e) culturing a product obtained in step (d) for a third period of time, in the absence of the at least one of the ascorbic acid and an analog thereof.

According to a second embodiment of the present invention for achieving the purpose above, there is provided:
a method of treating a subject afflicted with cardiac damage comprising:
(a) making a cell sheet comprising secondary spheroids, comprising:
(i) obtaining cardiosphere-derived cells;
(ii) cultivating the cardiosphere-derived cells for a first period of time in a first media comprising at least one of an ascorbic acid and an analog thereof, to form secondary spheroids;
(iii) transferring an amount of the spheroids formed in step (b) into a mold;
(iv) culturing the secondary spheroids for a second period of time in a second media comprising at least one of the ascorbic acid and an analog thereof, wherein the at least one of the ascorbic acid and an analog thereof is present in an amount effective to promote a formation of an extracellular matrix; and
(v) culturing a product obtained in step (d) for a third period of time, in the absence of the at least one of the ascorbic acid and an analog thereof;
(b) wrapping the obtained cell sheet around a balloon stent catheter;
(c) inserting the cell sheet-wrapped balloon stent catheter formed in step (b) into a coronary artery of the subject;
(d) inflating the balloon catheter to expand the stent; and
(e) deflating and removing the balloon catheter.

BRIEF DESCRIPTION OF THE DRAWINGS

Below, the invention is explained in more detail with reference to exemplary drawings, as follows:
FIGS. 11A-11F show representative histological images and data relating to characteristics of the cell sheet;

Figure 1:
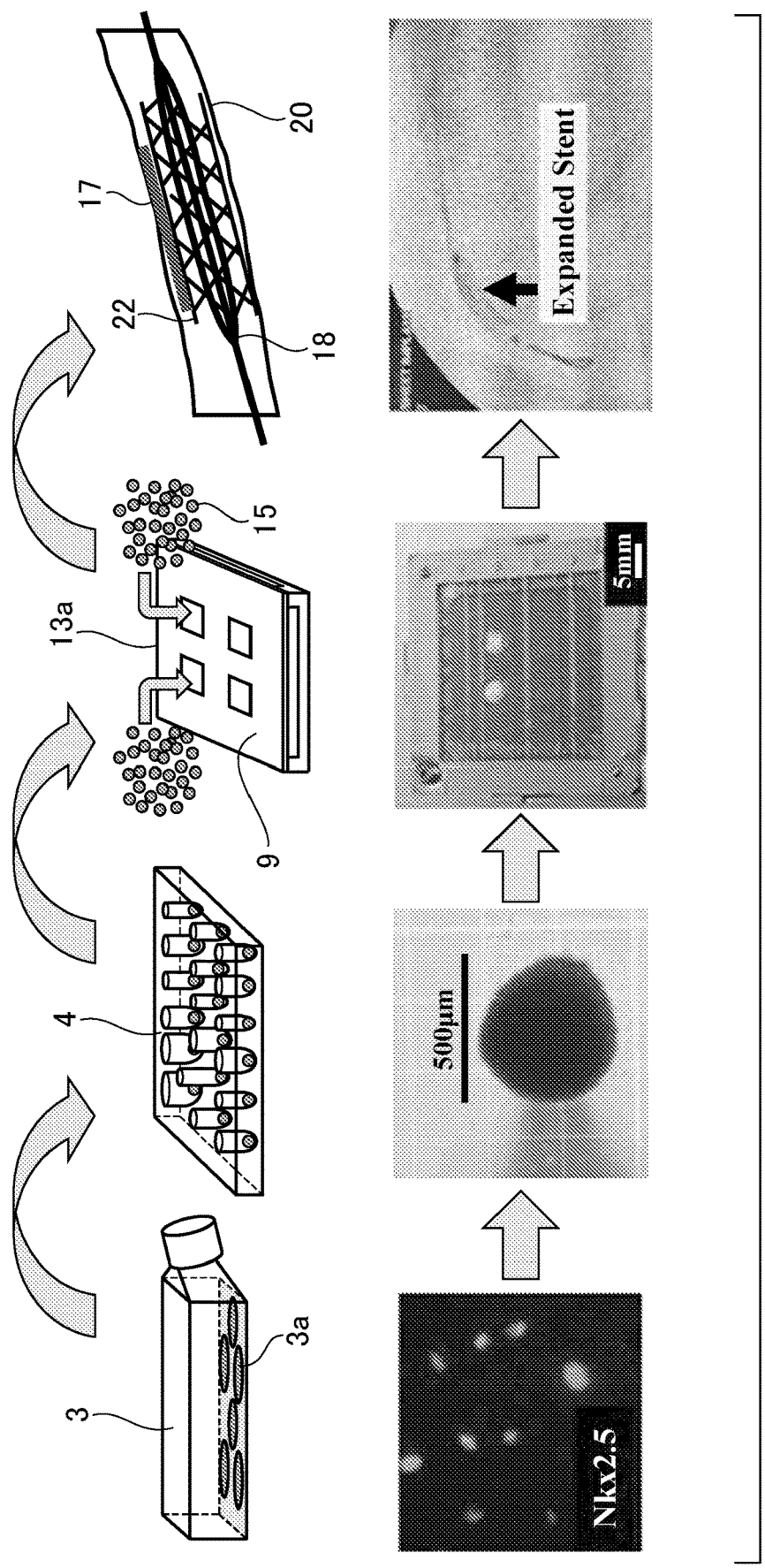
FIG. 1 shows a process for cell sheet formation and transplantation.

Other features and advantages of the present invention will become apparent from the following detailed description, taken in conjunction with the accompanying drawings, which illustrate, by way of example, the principles of the invention.

DETAILED DESCRIPTION OF THE INVENTION

In the following, preferred embodiments of the present invention will be explained. Numerical values are only examples for making it easier to understand the invention, and unless specifically indicated, do not limit the present invention. In this specification and drawings, the same reference numbers will be given to elements having essentially the same function, and any redundant explanations, as well as elements that are not directly related to the present invention, will be omitted.

Essentially, the present invention provides a cell sheet comprising secondary spheroids cultivated from cardiosphere-derived cells as described herein. The cell sheet may be used to treat cardiac damage by being placed inside a coronary artery, or more specifically, the cell sheet may be placed in the lumen of the artery. The cell sheet avoids the potential risks and drawbacks of existing biotechnologies, such as the use of CDCs or CDC monolayers, in cardiac regeneration.

The present invention involves such placement of the cell sheet in the coronary artery, in order to permit longer survival of the cell sheet than if the sheet was implanted in the pericardial heart. Epicardial placement of the cell sheet would require open chest surgery, causing greater stress for patients. On the other hand, if cardiospheres were injected directly into the coronary artery, they would clog the capillary network. If they were injected directly into the heart, they would not be retained for as long as in a cell sheet. The biotechnology of the present invention optimizes cell retention as well as prolonging paracrine secretion. Intraluminal cell sheet delivery without stent(s) is not practical because the construct is very fragile and may cause acute thrombus formation and micro-embolization of debris.

With the present invention, secondary cardiospheres fused with an extracellular matrix released from the cardiospheres, form flexible and durable cell sheets, without sacrificing abundant paracrine factor secretion, and while amplifying the stem cell mobilizing effects. Thus, the present invention creates thin, flexible and durable cell sheets containing viable stem cells that overcome the above-mentioned, potential risks.

Sample Collection, Processing and Characterization of Cardiosphere-Derived Cells (CDCs)

Porcine specimens were obtained from needle biopsies of the ventricular free wall. Tissue specimens were cut into 1-2 $mm^3$ pieces. After gross connective tissue was removed from fragments, tissue fragments were washed and partially digested enzymatically in a solution of type IV collagenase for 60 minutes at 37° C. The tissue fragments were cultured as "explants" on dishes coated with fibronectin. After a period of 8 or more days, a layer of stromal-like cells emerged from and surrounded the explants. Over this layer a population of small, round, phase-bright cells migrated. Once confluent, the cells surrounding the explants were harvested by gentle enzymatic digestion. These cardiosphere-forming cells were seeded at 2 to $3\times10^4$ cells/mL on poly-D-lysine-coated dishes in a cardiosphere medium (20% heat-inactivated fetal bovine serum, gentamicin 50 µg/ml, 2 mmol/L L-glutamine, and 0.1 mmol/L 2-mercaptoethanol in Iscove's modified Dulbecco medium). After a period of 4-10 days in culture, cardiospheres formed, detached from the tissue culture surface, and began slowly growing in suspension. When sufficient in size and number, these free-floating cardiospheres were harvested by aspirating them along with media. Cells that remained adherent to the poly-D-lysine-coated dishes were discarded. Detached cardiospheres were plated on fibronectin-coated flasks where they attached to the culture surface, spread out and formed a monolayer of "Cardiosphere-Derived Cells" (CDCs). 50-100 million CDCs were able to grow within 4-6 weeks of the time that the original cardiac tissue was obtained. CDCs were stored in the freezer (−80 degrees) until the creating of a cell sheet.

Figure 2:
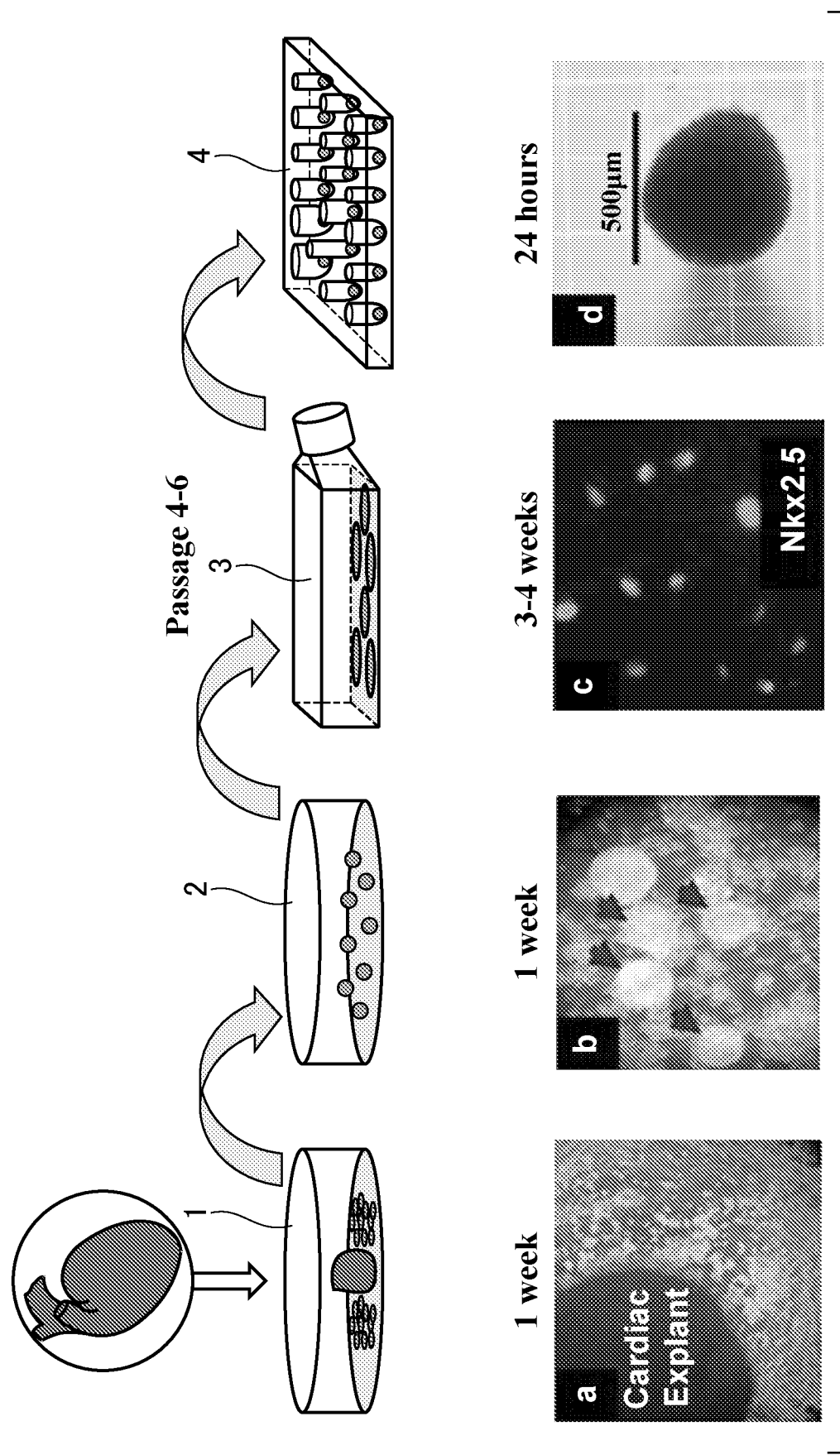
FIG. 2 shows a process for creating secondary cardiospheres from cardiac tissue.

The above-described process is shown in FIGS. 2 and 1, wherein cardiac tissue ("explant") was cultured on dishes coated with fibronectin. After one week, a layer of stromal-like cells started surrounding the explants 1 (image a shows the cardiac explant and outgrowth cells). Over this layer, a population of small, round, and phase-bright cells were detected. These cells were harvested and started forming cardiospheres 2 (image b shows the cardiospheres). The cardiospheres were collected and expanded on the fibronectin-coated dishes 3 (image c shows the cardiosphere-derived cells 3a). Equal amounts of cells were plated into ultra-low attachment round-shaped plates to create 2nd cardiospheres of the same size 4 (image d shows the 2nd cardiospheres).

Figure 3:
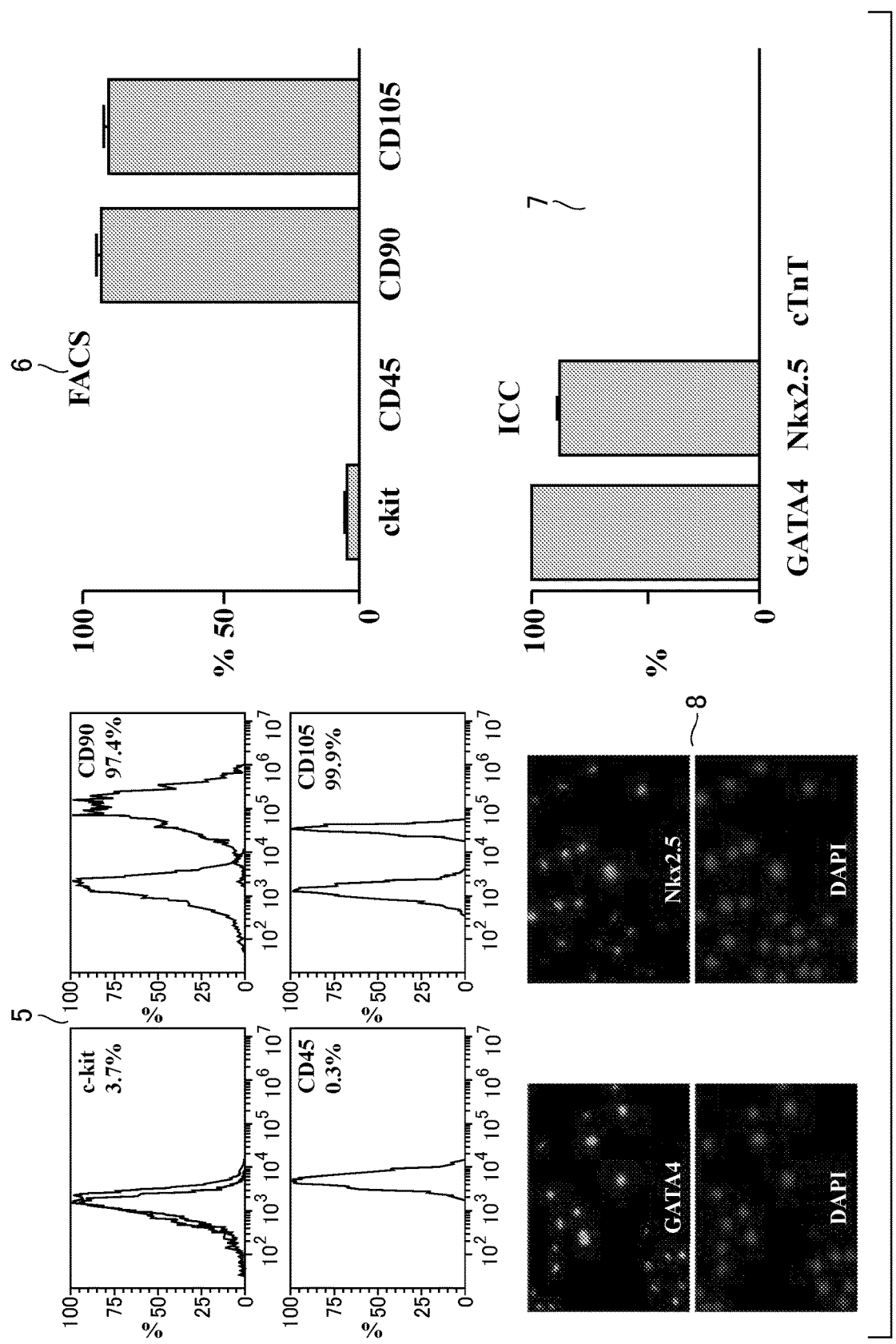
FIG. 3 illustrates data for CDCs expressing early cardiac markers.

Since CDCs express heterogeneous cell markers (cKit: stem cell, CD90/CD105: mesenchymal cell, GATA4/Nkx2.5: early cardiac myocyte), they are a mixture of stem cells and cardiac progenitor cells committed to a cardiac fate. FIG. 3 shows the characterization results and representative images supporting that the CDCs expressed early cardiac markers. CDCs at passage 6 prior to injection were characterized. The CDCs had a low rate of c-kit positivity (~5%) and over 95% expressed mesenchymal markers (see 5 and 6 in FIG. 3). The CDCs were exclusively positive for myocyte transcription factors (GATA4: 100%; and Nkx2.5: 94%, as shown at 7 and the representative images at 8 in FIG. 3); but, were negative for hematopoietic and cardiac (cTnT and cTnI) markers (see 7 in FIG. 3). Thus, the data indicates that the CDCs were committed to an early cardiac progenitor line.

Mold System for Generating Cardiosphere-Based Cell Sheet (Optimization of Cardiosphere Size)

The below description of a possible embodiment of the invention explains how thin, flexible, and durable cardiosphere-based stem cell sheets using a cell sheet mold that utilizes extracellular matrix released from cardiospheres, were produced.

The CDCs were recovered from freezing and cultivated for 1 week before cell sheet production. Cell suspensions (a total cell count of $2.0\times10^4$) was plated into each well of ultra-low attachment round-shaped 96-U-well plates (from the Sumitomo Bakelite Co. Ltd. of Tokyo, Japan), and filled with cardiosphere medium (20% heat-inactivated fetal bovine serum, gentamicin 50 µg/ml, 2 mmol/L L-glutamine, and 0.1 mmol/L 2-mercaptoethanol in Iscove's Modified Dulbecco Medium), 40 ng/ml basic fibroblast growth factor and 4 ng/ml ascorbic acid, as would be known to those with ordinary skill in the art. After 24 hours, the cells aggregated to form a round shaped cardiosphere (2nd cardiospheres).

It should be noted that the cardiosphere medium can include ascorbic acid or an analog thereof. Such analogs may include but are not limited to ascorbic acid 2-phosphate, ascorbic acid 3-phosphate, as well as salts and hydrates thereof, such as Mg and Mg hydrate. Such media may also include an amount of a growth factor effective to promote growth of the cardiosphere-derived cells, such as basic fibroblast growth factor.

Figure 5:
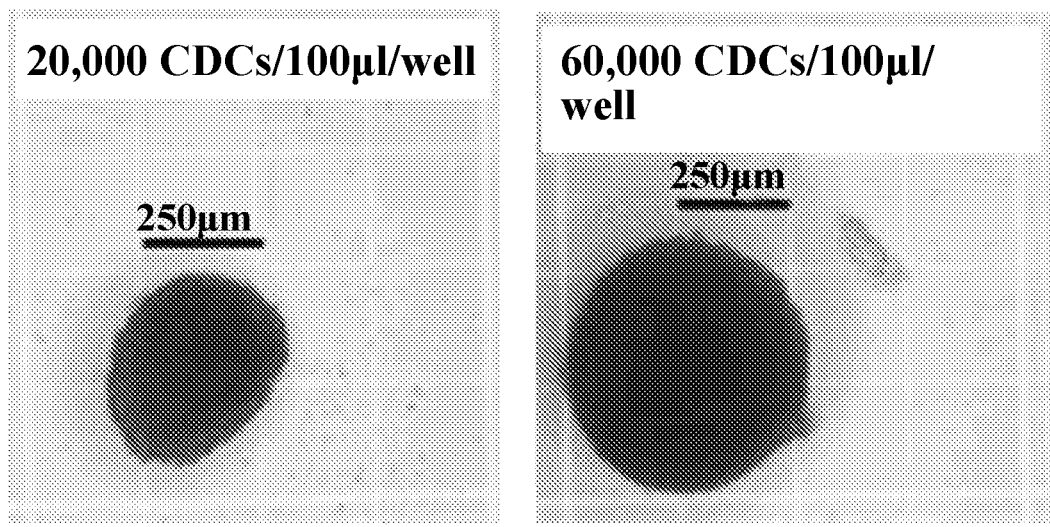
FIG. 5 shows an example of numbers of CDCs and sizes of the cardiospheres.

FIG. 5 shows the number of CDCs and the size of the cardiospheres. That is, in order to optimize the cell number for each sphere, CDCs from 4 donor animals were tested at different concentrations ($2.0 \times 10^4$, $6.0 \times 10^4$, $2.0 \times 10^5$ cells/100 µL) and sphere size was measured. As mentioned above, the cells were plated into ultra-low attachment round-shaped 96-U-well plates. Within 24 hours, the spheres were formed and their sizes were measured by a hemocytometer grid, with the results as displayed in FIG. 5.

Figure 4A:
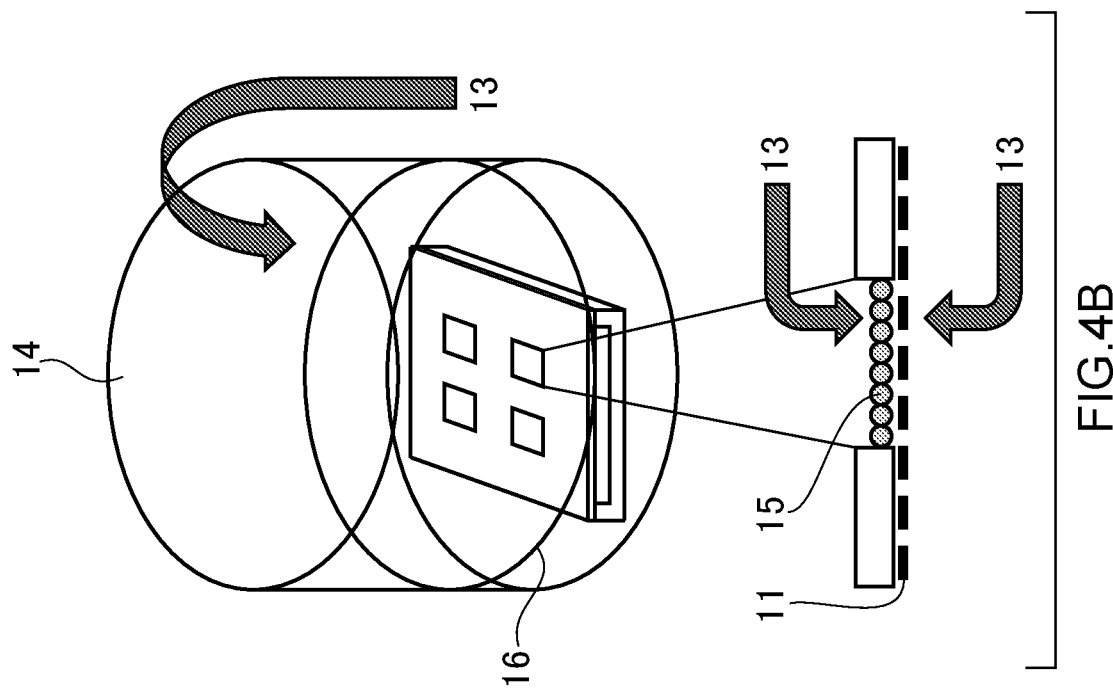
FIGS. 4A-4B show an example of a cell sheet mold, where the top 2 images show the mold and the mold immersed in media, and the bottom 2 images show their respective side views.
Figure 4B:
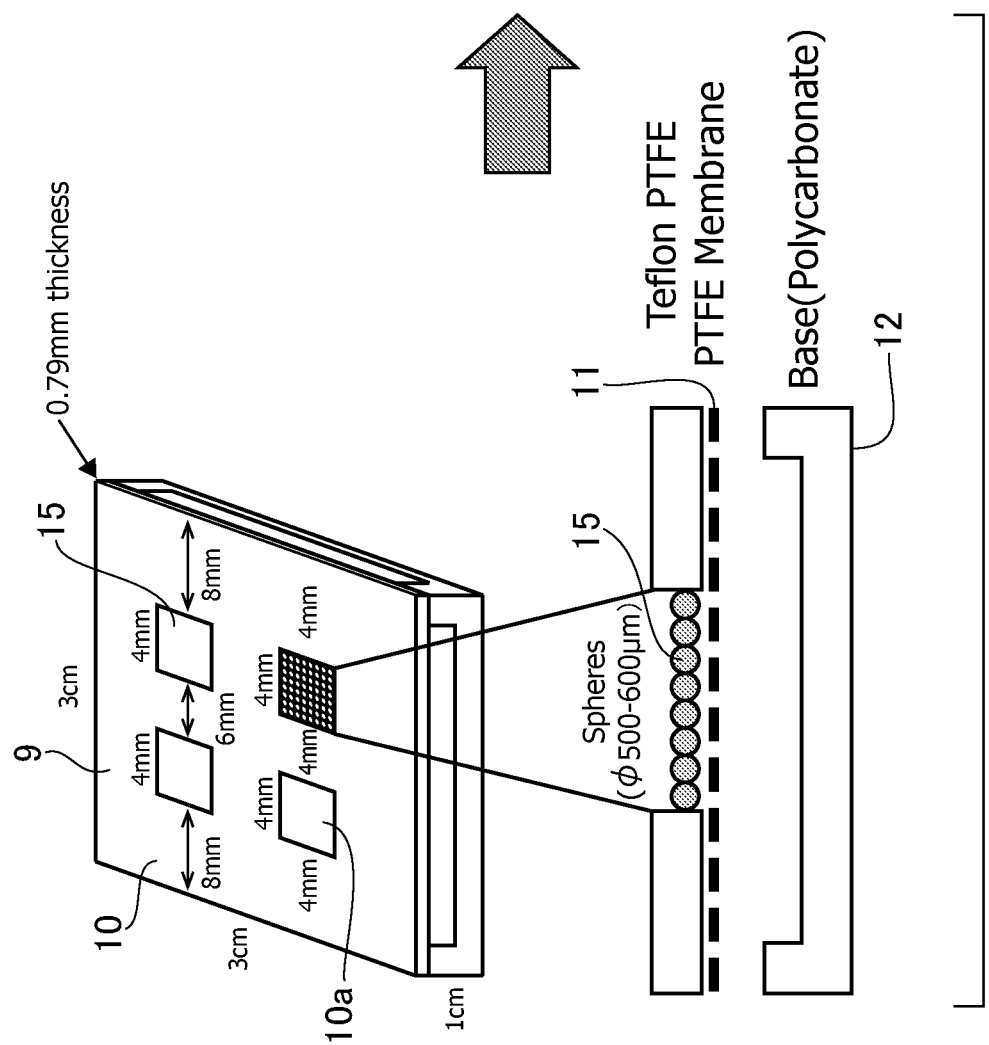

As shown at FIGS. 4A and 4B, the cardiospheres (~200 spheres) were placed onto a mold 9 and cultured for 7 days. In a possible embodiment, a top layer 10 of the cell sheet mold 9 is made of a low adhesion material such as Teflon™ PTFE (0.79 mm thickness), and the mold also includes a membrane 11 made of a low adhesion material such as PTFE with 5 µm pores, and a polycarbonate base 12. It should be noted that the pore sizes may typically range anywhere from 4 µm to 10 µm, in order to permit the circulation of the media. The top layer 10 has at least one aperture 10a, at which the cardiospheres (~200 spheres) at placed. Since the aperture 10a provides an opening and the PTFE membrane has tiny pores, the culture media 13 can circulate from the top and bottom parts of the cell sheet. For the first 3 days bFGF (10 ng/ml) and L-ascorbic acid 2-phosphate (L-AA, 20 µg/ml) were added to basal IMDM media containing 20% FBS, 2 mmol/L GlutaMAX, 10000 U/ml of penicillin and streptomycin and 0.1 mmol/L of β-mercaptoethanol. bFGF helps to keep the cells small in size and dividing. L-AA enhances the secretion of the extracellular matrix, which helps to bind the spheres together. At day 4, the bFGF and L-AA were removed and the cardiospheres were cultured until day 7.

In operation, as depicted in FIG. 4B and at 13a of FIG. 1, the mold 9 is immersed in media 13 inside a container 14. The media 13 is filled in up to a level 16 above the top level of the mold 9. Then, the media 13 circulates through the membrane 11 by diffusion as shown by the arrows in the side view of FIG. 4B. The membrane 11 may typically have a pore size ranging anywhere from 4 to 10 µm. Independently of the pore sizes of the membrane 11, the top layer 10 may also typically have a pore size ranging anywhere from 4 to 10 µm. The top layer 10 may have, in a possible embodiment, four apertures 10a, wherein each aperture measures about 4 mm×4 mm, as a cell sheet template of 4 mm×4 mm.

It should be noted that, irregardless of the composition of the above-mentioned cardiosphere medium, this second media 13 in which the mold 9 is immersed can include ascorbic acid or an analog thereof. Such analogs may include but are not limited to ascorbic acid 2-phosphate, ascorbic acid 3-phosphate, as well as salts and hydrates thereof, such as Mg and Mg hydrate. Such media may also include an amount of a growth factor effective to promote growth of the cardiosphere-derived cells, such as basic fibroblast growth factor.

When the cell sheet formation is complete, the top layer can be picked up by forceps. The cell sheet itself can then be removed with forceps. This is a significant advantage over molds that require enzymatic action to remove the cell sheet. Use of such enzymes weaken or break cell sheets. One such mold needing enzymatic detachment utilizes collagen-coated PFTE. The present invention allows for the use of PTFE that is not coated with collagen for the mold, thereby avoiding the disadvantageous use of such enzymes.

The above process may produce a cell sheet consisting of secondary spheroids having a diameter of about 500 µm to about 1450 µm, including all ranges and integers therebetween. In other embodiments, the diameters of the secondary spheroids may range from 600 µm to about 1450 µm or be significantly greater than 600 µm to about 1450 µm, or all about 500 µm. The cell density that can be used to form spheroids of such a diameter is from about 60,000 to 200,000 cells/µl.

Figure 6A:
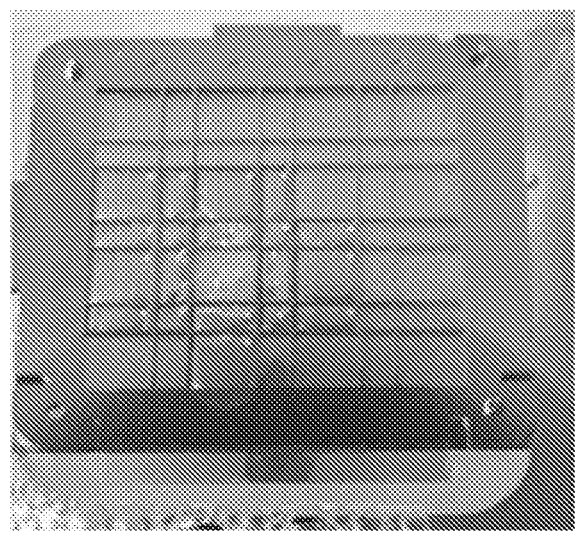
FIGS. 6A-6B illustrate an example of cell sheet creation using smaller sized cardiospheres.
Figure 6B:
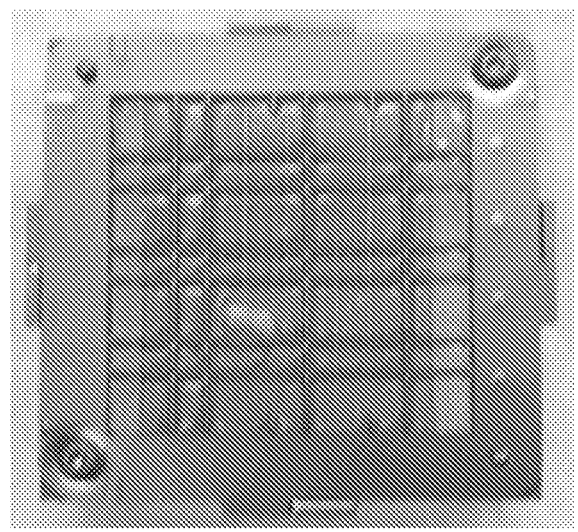

As described above relating to FIG. 5, in order to optimize the number of cells for creating a cell sheet, the CDCs were initially divided experimentally into $2.0 \times 10^4$, $6.0 \times 10^4$ and $2.0 \times 10^5$ cells per well, respectively. The corresponding sphere diameters were 370±37, 630±47 and 1450±42 µm, respectively. As described above, 200 $2^{nd}$ cardiospheres 15 were placed into the cell sheet mold. As a result, as shown in FIGS. 6A-6B, the cell sheet made from the $2.0 \times 10^4$ cells per well created a cell sheet that was half-size and the product was fragile. That is, FIG. 6A shows the spheres in the mold, and FIG. 6B shows the result 7 days after culture, in which the cell sheet had shrunk and was fragile in the mold.

Figure 7A:
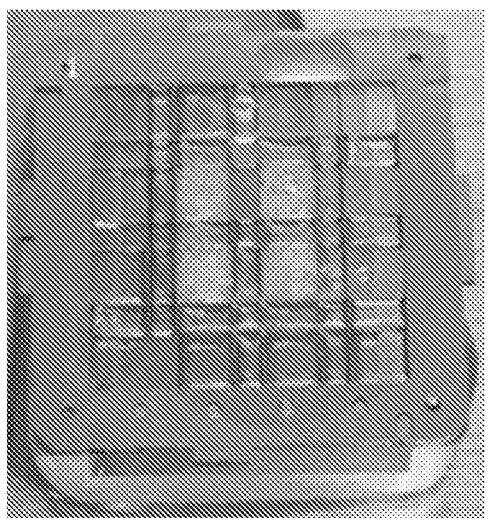
FIGS. 7A-7C illustrate an example of cell sheet creation using relatively larger sized cardio spheres.
Figure 7B:
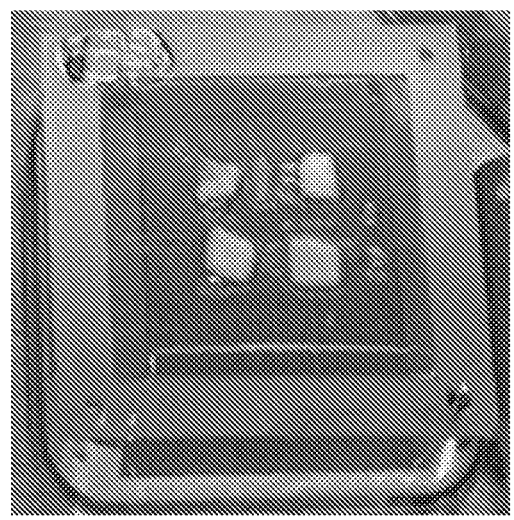
Figure 7C:
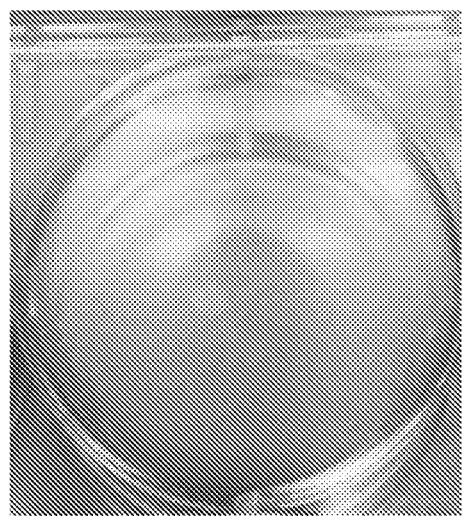

In contrast, cell sheets made from $6.0 \times 10^4$ and $2.0 \times 10^5$ cells per well filled in their space/apertures in the mold and the final products were flexible and durable, as shown in FIGS. 7A-7C (for the $6.0 \times 10^4$ cells per well). That is, FIG. 7a shows the spheres in the mold, and FIG. 7B shows the result 7 days after culture, in which the cell sheet was flexible and durable. The representative image of FIG. 7C shows the resulting cell sheet in a 6 well plate.

In the following explanation, secondary cardiospheres made at the concentration of over $6.0 \times 10^4$ cells per well (equal to 10-12 million of CDCs per sheet) were used.

Bio-3D Printer for Generating Cell Sheet of Cardiospheres

Figure 8A:
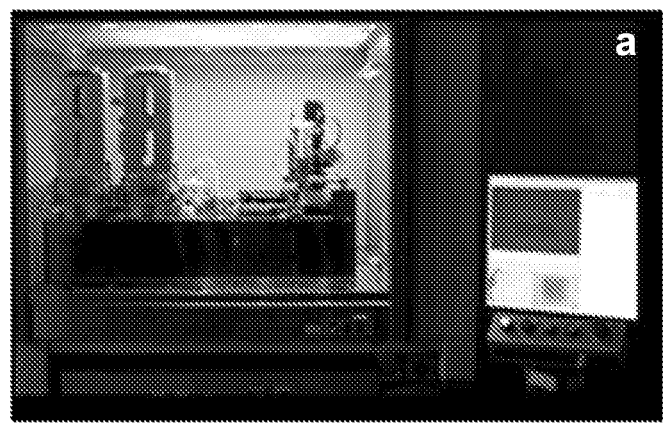
FIGS. 8A-8D show the structures and cardiospheres for 3D printing of a cell sheet.
Figure 8B:
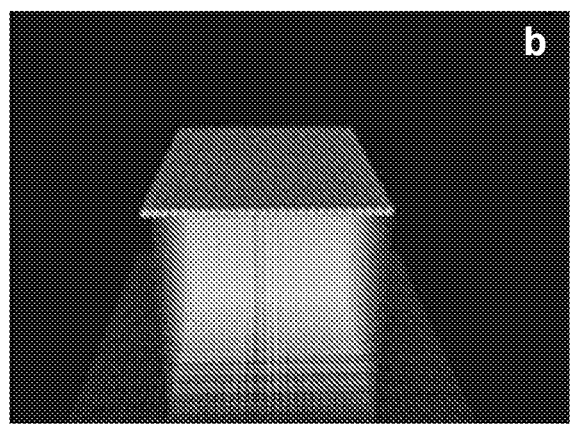
Figure 8C:
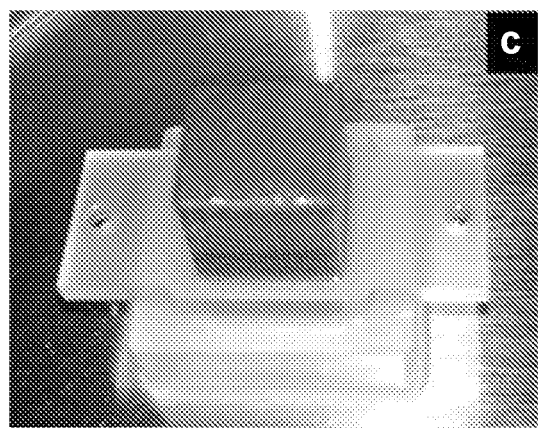
Figure 8D:
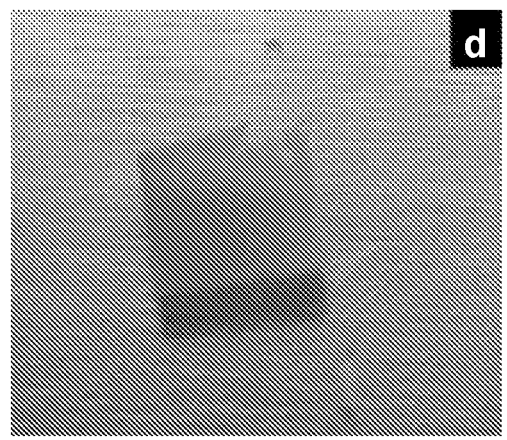

It is known that a "Bio-3D Printer" such as, for example, one manufactured by Cyfuse Biomedical K.K., Japan (FIG. 8A) may be used to assemble cardiospheres for constructing scaffold-free tissue, and this method was initially used for experimentation purposes. As shown in FIGS. 8A-8D, according to a three-dimensional structure predesigned on a computer system, the "Bio-3D Printer" skewered cardiospheres into a 26×26 needle-array (FIG. 8B). The outer diameter of each needle was 0.17 mm, and the distance between each needle was 0.4 mm. The size of the needle array was a square, 10.0 mm in length on each side (FIG. 8C). In this system, the cardiospheres were aspirated by a robotically controlled fine suction nozzle (O.D of 0.45 mm and I.D. of 0.23 mm) from the 96-well plate and inserted into the needle-array made of multiple medical-grade stainless needles. A total of 676 cardiospheres were placed into a 3D structure robotically according to the pre-designed configuration. The time required for the placement was approximately 1.3 hours. Seven days after the placement of the cardiospheres onto the needle-array, the needle-array was removed (FIG. 8D). A duration of seven days was chosen according to the results of our preliminary experiment, and the configuration of the structure was retained after the removal from the needle array due to fusion between and among the cardiospheres.

Cardiosphere-Based Cell Sheet Maintains Paracrine Function

As mentioned above, it has been demonstrated that myocardium regeneration induced by cardiosphere-derived cells (CDCs) mainly results from CDC secretions of paracrine factors, including growth factors, cytokines and microRNAs (examples include HGF, IGF-1, VEGF and SDF-1), rather than from direct differentiation of CDCs to de novo cardiac cells.

For the above reason, the paracrine factors from cardiospheres and cell sheets were compared to CDCs by qPCR analysis. It should be noted that the following referenced cell sheets are sheets made via the above-described method and mold system of the present invention, rather than being any scaffold-free tissue assembled via the above-described "Bio-3D Printer".

Figure 9:
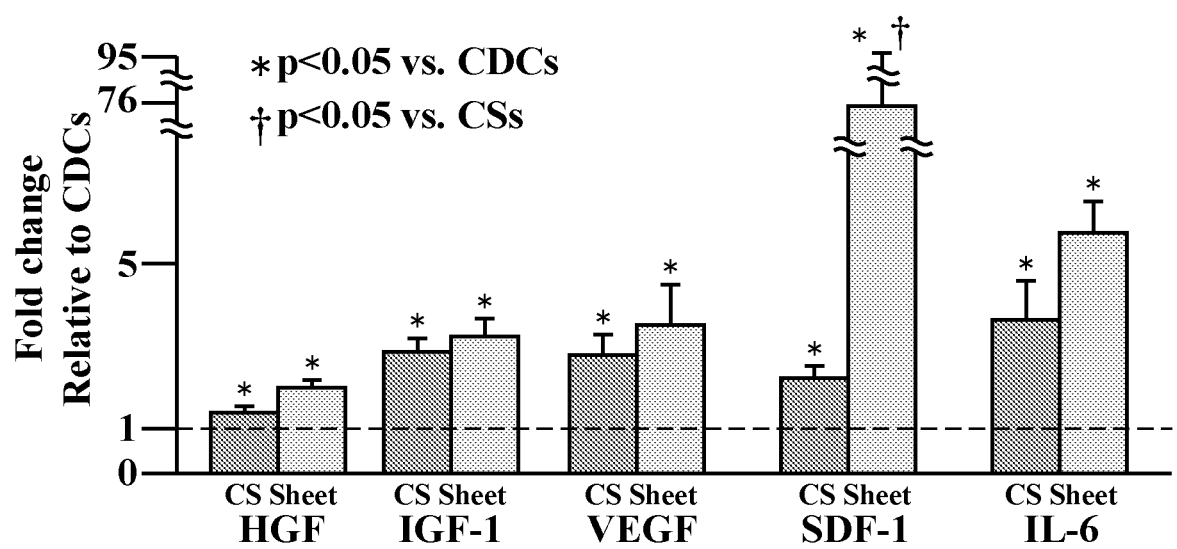
FIG. 9 illustrates data regarding paracrine factors of cardiospheres and cell sheet formation assessed by real-time quantitative polymerase-chain-reaction (qPCR) analyses.
Figure 10:
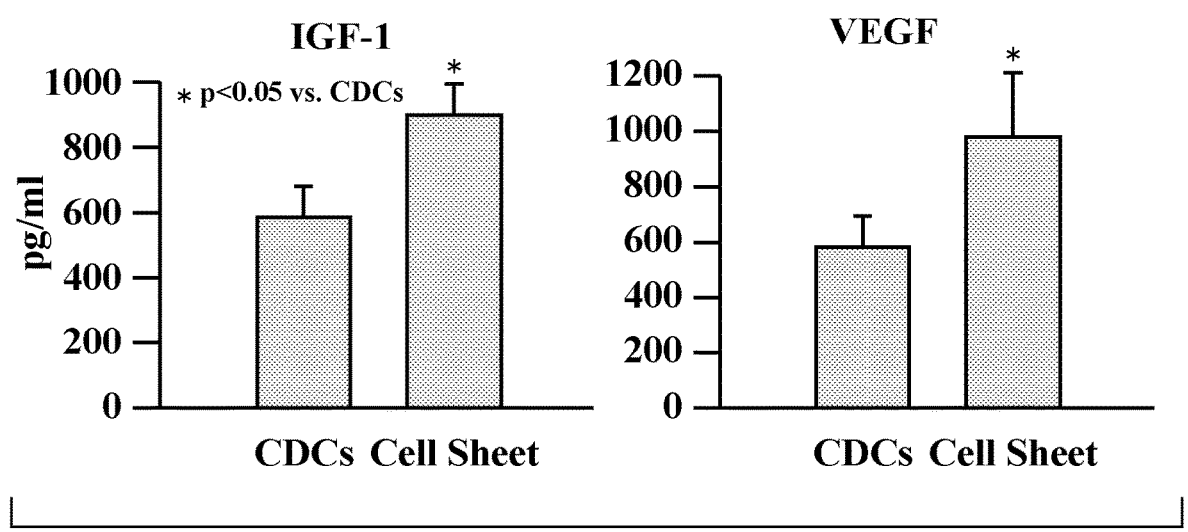
FIG. 10 illustrates data regarding protein expression of CDCs and the cell sheet.

The expression of major paracrine factors (HGF/IGF-1/VEGF/SDF-1/IL-6) which related to the angiogenesis was upregulated after cardiosphere formation. Those effects were maintained after cell sheet formation. In particular, SDF-1 which is related to stem/progenitor cell migration was significantly elevated in cell sheet, as presented in FIG. 9 (CS=Cardiospheres; Sheet=Cell Sheet). Moreover, in order to detect paracrine factor release from the cell sheet, the condition medium from the cell sheet was analyzed via ELISA (enzyme-linked immunosorbent assay). That data was compared to the data on the condition medium from CDCs, as shown in FIG. 10. The IGF-1 and VEGF protein levels from the cell sheet were significantly elevated compared to the CDC condition medium. Thus, cell sheet formation maintains the abundant paracrine factor secretion that the cardiospheres originally have, and cell sheet formation also amplifies the stem cell mobilizing effect.

Cell Sheet Maintains Stem Cell and Vascularization Capabilities

Figure 11A:
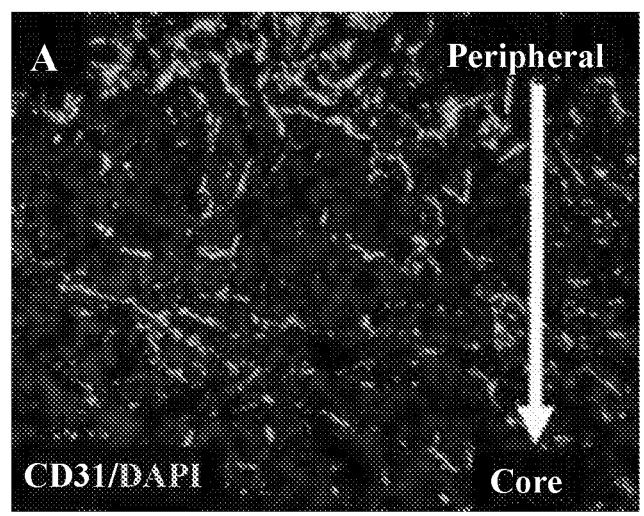
Figure 11B:
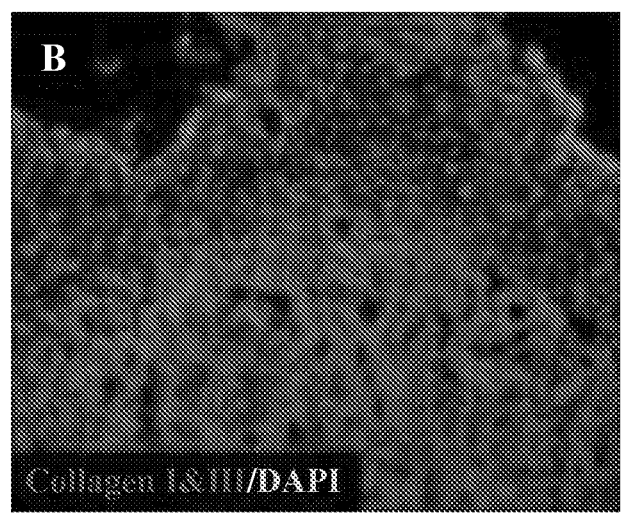
Figure 11C:
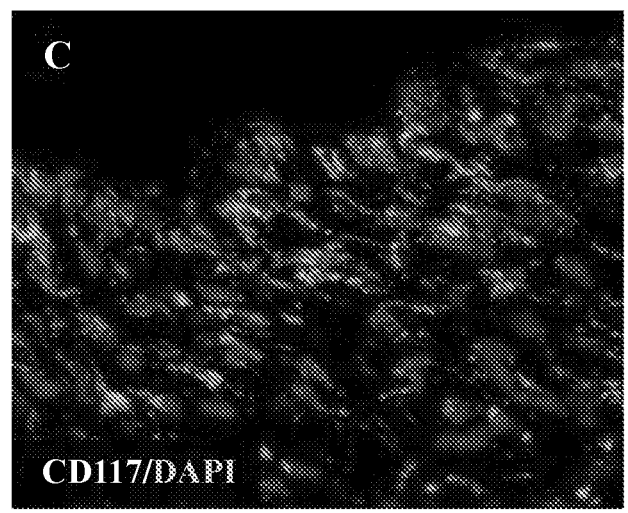
Figure 11D:
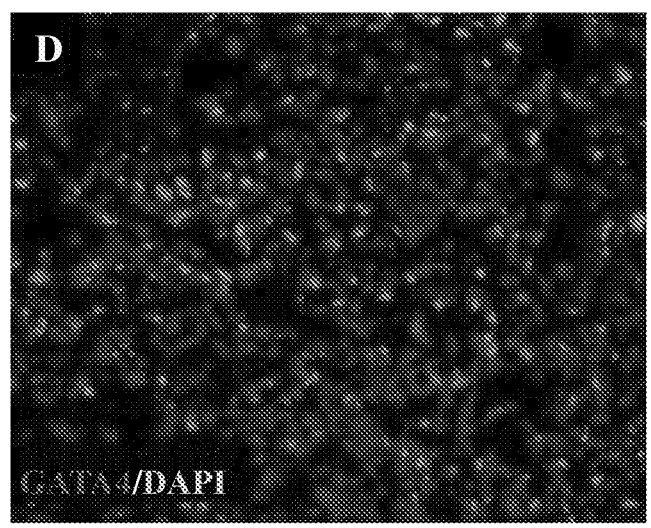
Figure 11E:
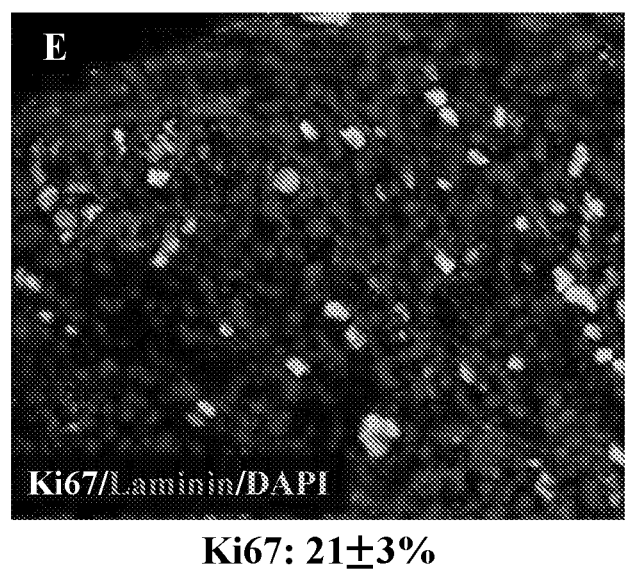

Immunohistological analysis demonstrated that the cell sheet consisted of stem/progenitor cells and capillary networks, as illustrated by the images of FIGS. 11A-E and the corresponding table of FIG. 11F. Each cell is fused with extracellular matrix which may tighten the cell sheet structure. CD31 positive capillaries, as shown in the image of FIG. 11A, that developed from the peripheral region to the core of the cell sheet. Extracellular matrix (collagen I&III), as shown in FIG. 11B, aggregate cardiospheres expressing stem cell markers (CD117/CD90, FIG. 11C). They express early myocyte (GATA4) and cell cycling markers (Ki67) as shown in FIGS. 11D and 11E. The cell sheet is well-vascularized, which may enhance cell survival, and maintains stem cell ability. The cell sheet does not express fibrosis, matured endothelial (vWF), smooth muscle markers ($\alpha$-SMA), cardiac muscle cells (cTnI) or apoptosis (TUNEL). Accordingly, one concludes that the bioengineered cell sheet successfully maintains the biological properties of cardiospheres and secretes abundant paracrine factors (e.g. HGF, IGF-1, VEGF and SDF-1). Histological analysis demonstrates that the cell sheet maintains stem cell ability.

Method to Deliver the Cell Sheet Inside of a Coronary Artery in Chronic Myocardial Infarction The following describes the successful deployment of the cell sheet of the present invention, into a coronary artery lumen. Yorkshire pigs (nominal weight 30 kg, female, n=17) were used to create myocardial infarction (MI) by an ischemia-reperfusion procedure (2-hour LAD occlusion and reperfusion). A balloon angioplasty catheter sized to match the mid left anterior descending artery or LAD (~2.5 mm×12 mm) was advanced and inflated distal to the second diagonal branch of the LAD for 120 minutes. At 1-month post-MI, an initial physiological study was performed. Those studies included angiographic assessment of the coronary arteries, LV function, hemodynamics analysis and 2D echocardiograms to measure global (Ejection Fraction (EF)) and regional (wall thickening) cardiac function. Three days before cell sheet administration, all of the animals were pre-treated with clopidogrel (300 mg orally) followed by daily aspirin (325 mg) and clopidogrel (75 mg). After the initial physiological studies, the animals were treated with intraluminal implantation of the cell sheet within a stent (cell sheet, containing $10 \times 10^6$ cells, n=5), intracoronary injection of CDCs ($10 \times 10^6$ cells, n=6) and saline (untreated, n=6).

Figure 12A:
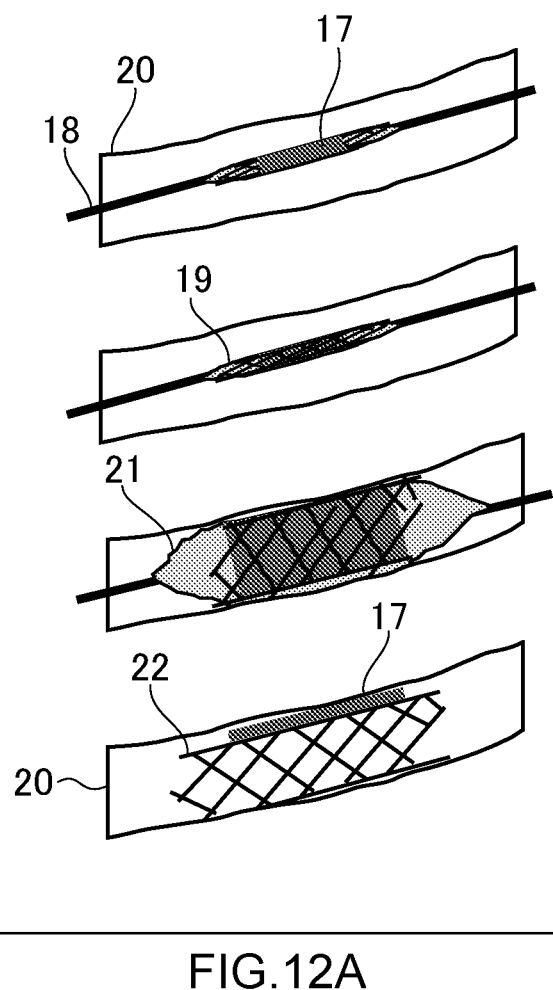
FIGS. 12A and 12B illustrate a process for cell sheet delivery.
Figure 12B:
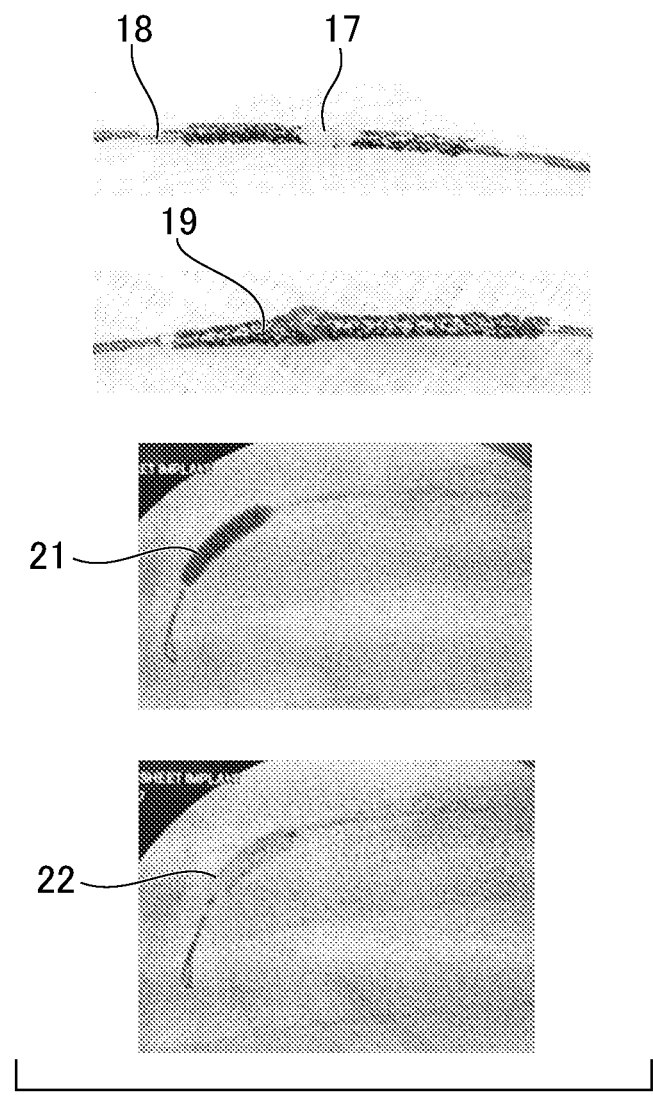

As illustrated in FIGS. 12A and 12B, in preparation for implantation, the cell sheet 17 (4 mm×4 mm×0.5 mm in size, containing ~$10 \times 10^6$ cells) was mounted and wrapped around a deflated stent balloon catheter 18 (FIGS. 12A and 12B). In another embodiment of the present invention, it is also possible to further insert the cell sheet-wrapped balloon stent catheter inside a second stent to form an assembly 19. In the mid LAD 20, the stent balloon was inflated to hold the cell sheet within the coronary artery, as shown by the inflated balloons 21 in FIGS. 12A and 12B. The successful dilation of stent(s) was confirmed by angiography. Then, the stent balloon 18 was deflated (see FIG. 1) and the catheter was removed, leaving the expanded stent(s) 22 to support and hold the cell sheet 17 within the coronary artery 20.

FIG. 1 shows in summary, with a process illustration and corresponding images, the present invention's full process for cell sheet formation and transplantation, including the cultivation of secondary spheroids from cardiosphere-derived cells 3a, the formation of the cell sheets in the mold 9, and the deployment of the cell sheet 17 in the mid LAD 20.

Microembolization and acute thrombus due to cell sheet implantation were assessed through the collection of blood samples at initial (day 0), 1 day, 3 days, 1 week and 2 weeks post implantation and the analysis of cardiac Troponin I (cTnI) and CK-MB. 2D echocardiograms (Ejection Fraction, wall thickening) were performed to confirm no functional impairments after the therapy. At 1-month post therapy, a final physiological study (hemodynamics, angiography and 2D echocardiogram) was performed and the hearts were excised for histology and protein analyses.

Figure 14A:
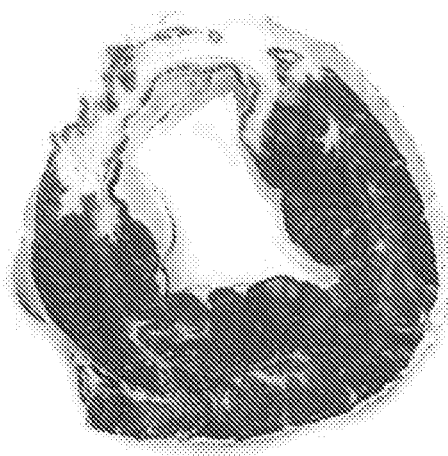
FIGS. 14A-14D illustrate the regenerative effects of the intraluminal cell sheet in cardiac myocardial infarction.
Figure 14B:
Figure 14C:
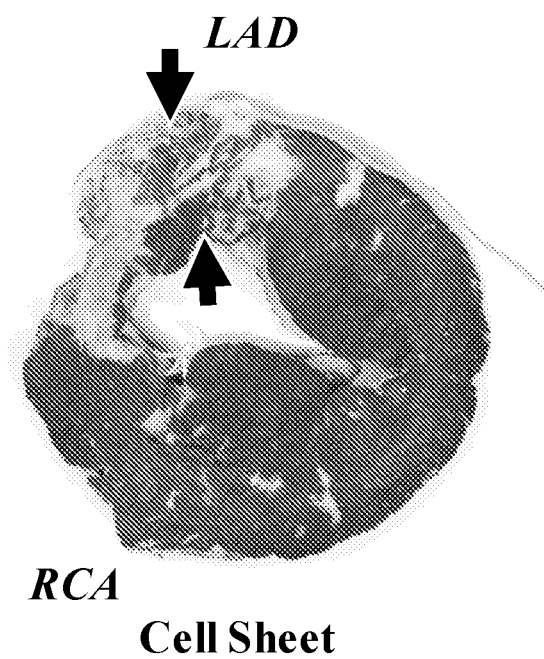
Figure 14D:
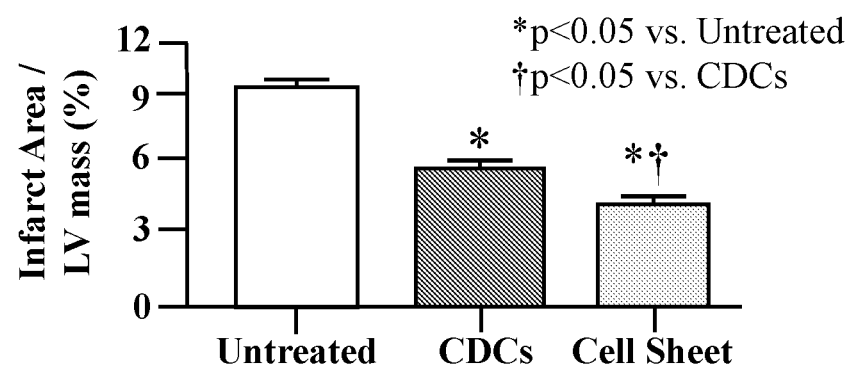

Functional Effects of the Intraluminal Cell Sheet in Cardiac Myocardial Infarction FIGS. 14A through 14C and the corresponding graph of FIG. 14D demonstrate that therapy with the cell sheet of the present invention promotes scar reduction and new myocyte generation. That is, at 1-month after myocardial infarction (MI), the infarct region had increased as assessed by post-mortem triphenyltetrazolium chloride (TTC) analysis (9.4±1.0%, FIG. 14A). However, after the intracoronary infusion of CDCs, the infarct size significantly decreased (5.3±0.6%, $p<0.05$ vs. Untreated, FIG. 14B). After therapy using the cell sheet, the infarct size significantly decreased and the viable mass in the middle of the infarct region (as indicated by arrows in FIG. 14C) had increased (3.6±0.4%, $p<0.05$ vs. Untreated and CDCs, respectively.) Thus, the data indicates that intraluminal cell sheet delivery promotes infarct scar size reduction, as well as promoting the generation of newly formed myocardium.

Figure 13:
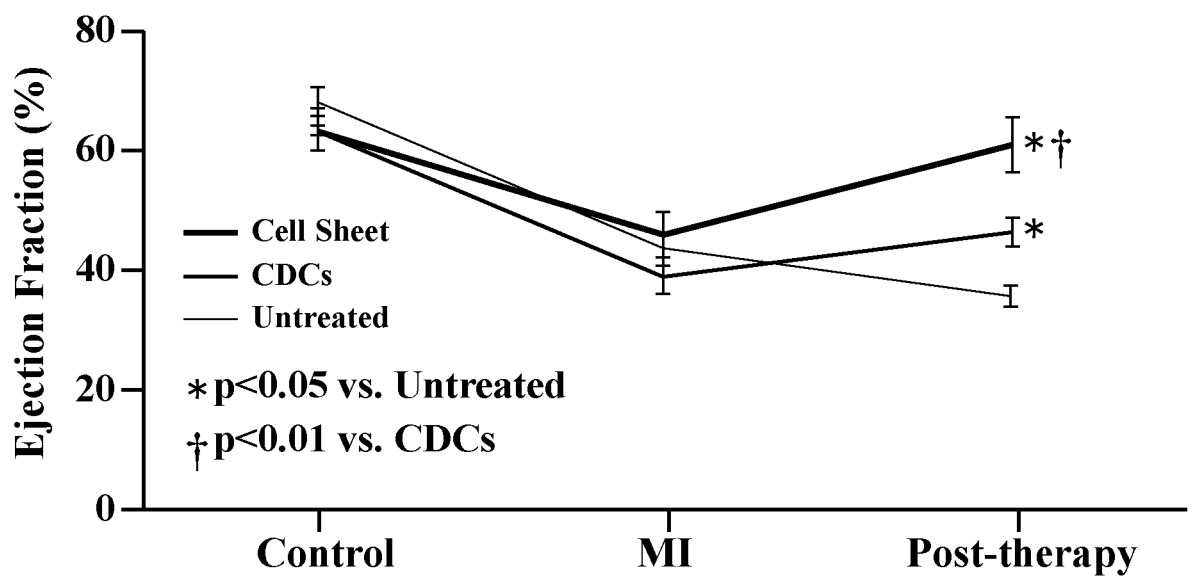
FIG. 13 illustrates data regarding the intraluminal cell sheet contrasted with standard intracoronary infusion of CDCs.

Furthermore, as also plotted on the graph of FIG. 13, at 1-month after myocardial infarction, cardiac function was significantly reduced as compared to the normal control (EF: 45±2% in MI vs. 62±1% in control, $p<0.05$). The cell sheet was delivered inside of the LAD coronary artery for 1 month. After the cell sheet therapy, cardiac function was recovered and close to nearly normal function (EF: 61±5%, n=5, p<0.05 vs. CDCs or Untreated, respectively). In contrast, intracoronary infusion of CDCs tended to preserve cardiac function after therapy (EF: 47±2%, n=6), p<0.05 vs. Untreated) and untreated animals showed deteriorated cardiac function (EF: 36±1%, n=6). Accordingly, the data indicate that intraluminal cell sheet delivery is a more beneficial therapy than the standard intracoronary infusion of CDCs. Accordingly, the above results show that therapy using the cell sheet of the present invention is more effective than standard cell therapies.

As demonstrated above, the cell sheet promoted remarkable functional improvements and scar reductions accompanied by a newly formed myocardium at 1-month post implantation. The therapeutic effect is significantly better than the effects from the intracoronary injection of stem cell delivery approach (representing one of the standard cell injection methods). The elevation of serum cardiac Troponin I was minimal (less than 0.02 ng/µl) after cell sheet implantation. Thus, collectively, the above-described intraluminal implantation has been demonstrated to be safe and feasible without causing any acute occlusion, thrombosis formation or micro-embolization of cell sheet debris. Furthermore, such intraluminal cell sheet delivery has more promising effects than standard cell-therapy in myocardial ischemia.

It is to be understood that the above-described embodiments are illustrative of only some of the many possible specific embodiments which can represent applications of the principles of the invention. Numerous and varied other arrangements can be readily devised by those skilled in the art without departing from the spirit and scope of the invention.

What is claimed is:

1. A method of making a cell sheet, comprising:
   obtaining a plurality of cardiosphere-derived cells;
   cultivating the cardiosphere-derived cells for a first period of time in a first medium comprising at least one of an ascorbic acid and an ascorbic acid analog thereof, to form a plurality of secondary spheroids, wherein the secondary spheroids have a diameter which is greater than 600 µm and not larger than 1450 µm;
   transferring an amount of the secondary spheroids into a mold;
   culturing the amount of the secondary spheroids in the mold, to obtain secondary spheroids fused with an extracellular matrix, for a second period of time in a second medium comprising the at least one of the ascorbic acid and an ascorbic acid analog thereof, wherein the at least one of the ascorbic acid and an ascorbic acid analog thereof in the second medium is present in an amount effective to promote a formation of the extracellular matrix to which the secondary spheroids fuse; and
   culturing the secondary spheroids fused with the extracellular matrix for a third period of time to obtain a cell sheet, in a medium that does not contain ascorbic acid and an ascorbic acid analog thereof,
   wherein the first medium and the second medium include a basic fibroblast growth factor in an amount effective to promote the growth of the cardiosphere-derived cells or the secondary spheroids, and wherein the ascorbic acid analog includes at least one of ascorbic acid 2-phosphate, an ascorbic acid 2-phosphate salt thereof, a hydrate of the ascorbic acid 2-phosphate salt, ascorbic acid 3-phosphate, an ascorbic acid 3-phosphate salt thereof, and a hydrate of the ascorbic acid 3-phosphate salt.

2. The method of claim 1, wherein the first period of time is about 24 hours.

3. The method of claim 1, wherein the second period of time is about 3 days.

4. The method of claim 1, wherein the third period of time is about 4 days.

5. The method of claim 1, wherein a total of the second period of time and the third period of time is about 7 days.

6. The method of claim 1, wherein the cardiosphere-derived cells obtained have a concentration of between $6.0 \times 10^4$ to $2.0 \times 10^5$ cells/100 µL.

7. The method of claim 1, wherein the mold comprises:
   a top layer having a shape of a flat sheet comprising at least one aperture;
   a base; and
   a membrane positioned between the top layer and the base such that the membrane covers the at least one aperture, and
   the amount of the secondary spheroids is cultured on the membrane within the at least one aperture.

8. The method of claim 7, wherein at least one of the top layer and the membrane comprises a non-collagen coated PTFE.

9. The method of claim 7, wherein at least one of the top layer and the membrane has a pore size of 4 µm to 10 µm.

10. The method of claim 7, wherein:
    the membrane includes pores positioned below the at least one aperture, and
    the culturing of the amount of the secondary spheroids includes circulating the second medium in the mold, via diffusion of the second medium through the pores.

11. The method of claim 7, wherein the top layer comprises four apertures, and each aperture of the four apertures is about 4×4 mm.

12. The method of claim 1, wherein the first medium includes at least one of Mg salt of ascorbic acid 2-phosphate, Mg hydrate of ascorbic acid 2-phosphate, Mg salt of ascorbic acid 3-phosphate, and Mg hydrate of ascorbic acid 3-phosphate.

* * * * *